United States Patent [19]

Cesark et al.

[11] 4,351,956

[45] Sep. 28, 1982

[54] OXIME ETHERS OF 4,4'-BIS(N,N-DIETHYLAMINO)BENZHYDROL AND PRESSURE-SENSITIVE RECORDING SYSTEMS CONTAINING THEM

[75] Inventors: Frank F. Cesark; Daniel W. Thomas, both of Bridgewater, N.J.

[73] Assignee: American Cyanamid Company, Stamford, Conn.

[21] Appl. No.: 297,802

[22] Filed: Aug. 31, 1981

[51] Int. Cl.³ .................... C07C 131/00

[52] U.S. Cl. .................... 564/256; 282/27.5

[58] Field of Search .................... 564/256; 427/150; 8/605; 428/323, 914; 282/27.5

[56] References Cited

U.S. PATENT DOCUMENTS

| | | | |
|---|---|---|---|
| 4,124,227 | 11/1978 | Russ | 564/256 |
| 4,238,130 | 12/1980 | Burri | 282/27.5 |

*Primary Examiner*—Natalie Trousof

*Assistant Examiner*—L. Hendriksen

*Attorney, Agent, or Firm*—Bruce F. Jacobs

[57] ABSTRACT

Compounds of the formula:

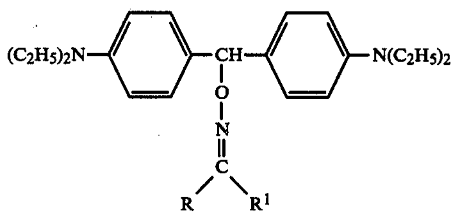

wherein R and $R^1$ are alkyl $C_1$–$C_4$ are useful as color formers for pressure- and heat-sensitive copying materials.

2 Claims, No Drawings

OXIME ETHERS OF 4,4'-BIS(N,N-DIETHYLAMINO)BENZHYDROL AND PRESSURE-SENSITIVE RECORDING SYSTEMS CONTAINING THEM

The present invention relates to compounds represented by the formula:

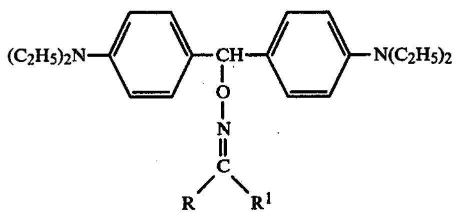

wherein R and $R^1$, which may be the same or different, represent an alkyl group of 1 to 4 carbon atoms; and to their use in pressure- and heat-sensitive copying material containing them as a part of their color reactant system.

Considerable investigation has been directed over the past years to the development of color former compounds for pressure- and heat-sensitive copying materials. Many of these have been various derivatives of Michler's hydrol-4,4'-bis(N,N-dimethylaminophenyl)-carbinol. Research continues in an effort to find improved color former compounds, that is, those having greater color intensity, which exhibit limited or no "ghosting" (multiple imaging related to sublimation), which have improved solubility properties, or are less expensive.

Ruus, U.S. Pat. No. 4,124,227, describes the use of compounds represented by the formula:

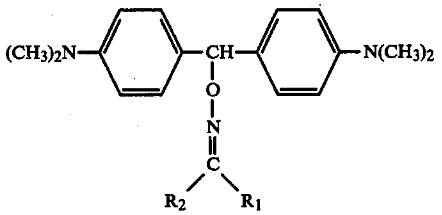

wherein $R_1$ and $R_2$ each represent an organic radical and, more specifically, $R_1$ may be either a lower alkyl group having 1 to 5 carbon atoms or a phenyl group, and $R_2$ represents a substituted or unsubstituted phenyl group of the formula:

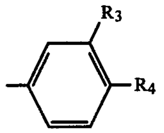

wherein $R_3$ and $R_4$ each separately represent a hydrogen atom, a chlorine atom, or a nitro group.

The compounds of the present invention differ structurally from those of Ruus in that they are prepared from the N,N-diethylamino analog of Michler's hydrol rather than from Michler's hydrol, and also in that they are prepared from aliphatic ketone oximes rather than aromatic ketone oximes.

The compounds of the present invention have advantages over the compounds of Ruus in that they are soluble in petroleum distillate solvents such as kerosine as well as produce good intensity. This is a distinct advantage in that most solvent systems used in the encapsulation of color former compounds are complex and expensive. Moreover, the compounds exhibit less "ghosting" than the analagous compounds based on Michler's hydrol.

The compounds are readily prepared by procedures similar to Ruus, that is, by reacting 4,4'-bis(N,N-diethylamino)benzhydrol with the appropriate ketone oxime compound in the presence of an acid, in accordance with the equation:

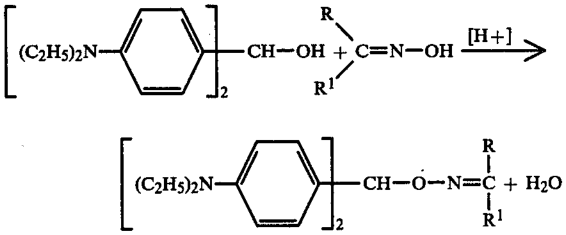

The oximes are readily prepared by treating an appropriate ketone with hydroxylamine hydrochloride in the presence of a base:

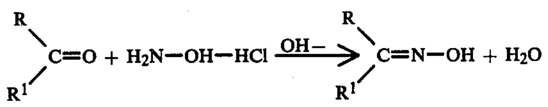

The preferred compound of the present invention is the actone oxime ether of 4,4'-bis(N,N-diethylamino)-benzhydrol.

The compounds of the invention are useful color formers when brought into contact with an acidic co-reactant substance which is electron accepting, that is, attapulgite clay, silton clay, silica, bentonite, halloysite clay, aluminum oxide, aluminum phosphate, kaolin, or any suitable acidic clay, or an acid-acting polymer, such as a phenolic resin, or a maleic acid rosin, partially or wholly hydrogenated polymer of maleic anhydride with styrene, ethylene, vinyl methyl ether, or carboxypolymethylenes. Preferred acidic co-reactants are attapulgite clay, silton clay, silica, and phenolic resins.

The compounds are used in pressure- and heat-sensitive copying and recording materials which comprise, for instance, at least one pair of sheets containing a color former compound and an acidic co-reactant substance. The color former compound is desirably dissolved in an organic solvent and is preferably contained in a pressure-rupturable microcapsule.

When the microcapsules containing the color former compound are ruptured by pressure, for example, and the color former is thus transferred onto an adjacent sheet coated with a substance capable of acting as an electron acceptor, a colored image is produced.

The general art of making microcapsules is well-known; see, for example, U.S. Pat. Nos. 2,183,053; 2,797,201; 2,800,457; 2,800,458; 2,964,331; 3,016,308; 3,171,878; 3,265,630; 3,405,071; 3,418,250; 3,418,656; 3,424,827; and 3,427,250.

Preferably, the color former compounds are encapsulated in an organic solvent. Suitable solvents include, but are not limited to, petroleum hydrocarbon distillates, such as kerosine; polychlorinated biphenyls, such as trichlorobiphenyl; alkylated derivatives of naphthalene or biphenyls, such as isopropylated naphthalene or isopropylated biphenyls; tricresylphosphate; di-n- butylphthalate and dioctyl phthalate; trichlorobenzene, nitrobenzene, trichloroethylphosphate; partially hydrogenated condensed aromatic hydrocarbons, and mixtures thereof. The color former compounds of the present invention are advantageously soluble in petroleum hydrocarbon distillates and these are preferred solvents. Especially preferred are the kerosine fractions.

The encapsulating material may be gelatine; see U.S. Pat. No. 2,800,457. Alternatively, the capsule may be made from an aminoplast resin or modified aminoplast resin; see British Pat. Nos. 989,264 and 1,156,725.

A preferred copying material set may be made by coating the backside of a transfer sheet with the encapsulated color former compound and the front side of a receiving or absorbent sheet with the electron accepting substance. Pressure-sensitive copying materials are described in U.S. Pat. Nos. 3,516,846; 2,730,457, 2,932,582; 3,427,180; 3,418,250; and 3,418,656.

The microcapsules are preferably fixed to the carrier sheets by means of a suitable adhesive. Since paper is the predominant carrier material, these adhesives are paper coating agents, such as gum arabic, polyvinyl alcohol, hydroxymethylcellulose, or dextrin.

The compounds of the invention may also be used in heat-sensitive copying materials, as described in U.S. Pat. No. 4,238,130.

The following examples, in which all parts are by weight, further illustrate the invention.

EXAMPLE 1

Preparation of 4,4'-Bis(N,N-diethylamino)benzhydrol, acetone oxime ether

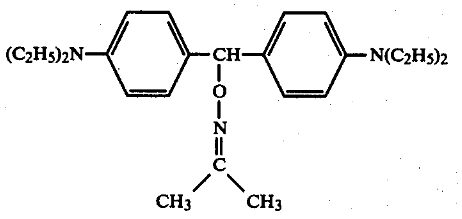

A mixture of 4,4'-bis(N,N-diethylamino)benzhydrol (11.0 grams, 0.034 mole), acetone oxime (2.66 grams, 0.036 mole), 50 ml of methylethyl ketone and 100 ml of n-hexane was brought to refluxing temperature and 10 drops of methanesulfonic acid was added. The reaction mixture was refluxed (65°-67° C.) for a period of about 1.5 hours, during which time 100 ml of distillate was removed and replaced with 60 ml of methylethyl ketone/n-hexane (1/1). The reaction mixture was filtered hot and the filtrate was cooled to −30° C. to −40° C. in dry ice to provide a white precipitate which was filtered at −30° C., washed with n-hexane and dried. The product was then dissolved in n-hexane (40 ml), filtered, and the filtrate reheated to 55° C. and re-cooled to 20° C. to provide a white solid which was filtered, washed with n-hexane and dried; mp 63.5°-65° C.

EXAMPLE 2

Preparation of 4,4'-Bis(N,N-dimethylamino)benzhydrol, acetone oxime ether

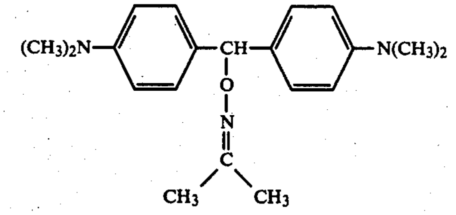

The procedure of Example 1 was followed except that 4,4'-bis(N,N-dimethylamino)benzhydrol was used. There was obtained a white solid material, mp 80°-81° C.

EXAMPLE 3

Preparation of 4,4'-Bis(N,N-diethylamino)benzhydrol, acetophenone oxime ether

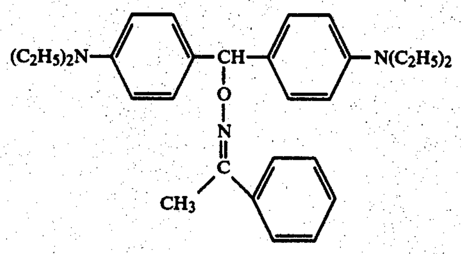

The procedure of Example 1 was followed except that acetophenone oxime was used instead of acetone oxime. There was obtained a solid material, mp 114°-115° C.

EXAMPLE 4

Preparation of 4,4'-Bis(N,N-diethylamino)benzhydrol, methylhexylketone oxime ether

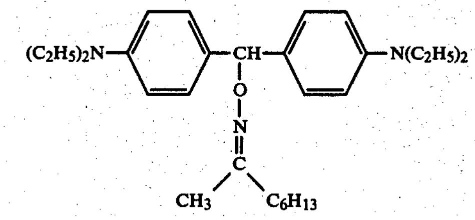

The procedure of Example 1 was followed except that methyl-n-hexylketone oxime was used instead of acetone oxime. There was obtained a yellow-orange oil.

EXAMPLE 5

To determine the effectiveness of the compounds of the invention as color formers and to compare them against the oxime ethers of Ruus, U.S. Pat. No. 4,124,227, the following tests were made.

Measurement of Image Intensity

A 220-screen quadragravure hand roller is used to evenly apply a 0.5% xylene solution of the color former-compound to resin coated color former paper. The visible reflectance spectrum is obtained with a General Electric-Hardy spectrophotometer. The λ max spectral value is transformed using Kebulka-Munk Theory to "k/s," reflectance for "infinitely thick" sample. The value obtained is compared with Crystal Violet Lactone (CVL) image value of 1.0. At least one CVL sample is included in each test series as a control. Reproducibility for the method has averaged 5% with 13% maximum deviation. Data are given in Table I.

Sublimation (Ghosting) Test Procedure

Ghosting observations are made by applying 5 drops of a 0.5% xylene solution of the color former compound to a 220-screen quadragravure hand roller and then evenly applying the solution to Reeve Angel filter paper (#201). The approximately 2"×4" center section of the drawdown is cut out. The solution side of the filter paper is placed in contact with the active side of a resin coated color former paper and the two sheets are placed in an Atlas Scorch Tester (ST-469, type SO-5A) and heated for 16 hours at 145°–150° F. The extent of color formed on the color former sheet is then visually estimated. Results are shown in Table I.

The data show that the compound of Ex. 1 (invention) is about equal in intensity to the compound of Ex. 2 (dimethylamino analog) but significantly better in resisting sublimation and soluble at 4% in kerosine. The compound of Ex. 3 (the diethylamino analog of Ruus) has poor color intensity, good sublimation resistance, but is insoluble in kerosine. The compound of Ex. 4 is slightly better in color intensity than the compound of Ex. 3 but much poorer than that of this invention, somewhat poorer in resistance to sublimation, but is soluble in kerosine.

TABLE I

| Compound of | Intensity k/s | Sublimation 16 Hrs at 145–150° F. | Solubility in Kerosine (4%) |
|---|---|---|---|
| Ex. 1 | 1.37 | trace-slight | soluble |
| Ex. 2 | 1.38 | moderate-considerable | insoluble |
| Ex. 3 | 0.95 | trace-slight | insoluble |
| Ex. 4 | 1.05 | slight-moderate | soluble |

What is claimed is:

1. The compounds represented by the formula:

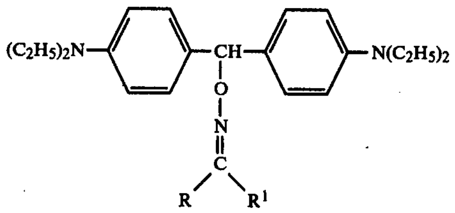

wherein R and $R^1$, which may be the same or different, represent an alkyl group of 1 to 4 carbon atoms.

2. The compound of claim 1 wherein R and $R^1$ are each methyl.

* * * * *